United States Patent
Pitts et al.

(10) Patent No.: US 9,250,191 B2
(45) Date of Patent: *Feb. 2, 2016

(54) METHOD FOR ANALYSING AMINO ACIDS AND A REAGENT FOR USE WITH THE SAME

(71) Applicant: JPP Chromatography Limited, Plymouth, Devon (GB)

(72) Inventors: Leslie John Pitts, Devon (GB); Michael Gerard Pallot, Devon (GB); Phillip Jones, Plymouth (GB)

(73) Assignee: JPP Chromatography Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/086,282

(22) Filed: Nov. 21, 2013

(65) Prior Publication Data

US 2014/0141520 A1 May 22, 2014

(30) Foreign Application Priority Data

Nov. 21, 2012 (GB) .................................. 1220906.0

(51) Int. Cl.
- *G01N 21/78* (2006.01)
- *G01N 33/68* (2006.01)
- *B01D 15/08* (2006.01)

(52) U.S. Cl.
CPC ................ *G01N 21/78* (2013.01); *B01D 15/08* (2013.01); *G01N 33/6806* (2013.01); *Y10T 436/10* (2015.01); *Y10T 436/108331* (2015.01); *Y10T 436/17* (2015.01); *Y10T 436/200833* (2015.01)

(58) Field of Classification Search
CPC ....... G01N 21/77; G01N 21/78; G01N 33/68; G01N 33/6806; Y10T 436/10; Y10T 436/107497; Y10T 436/108331; Y10T 436/143333; Y10T 436/17; Y10T 436/200833; Y10T 436/201666; Y10T 436/202499; Y10T 436/203332; Y10T 436/204165; Y10T 436/25

USPC ............... 436/8, 17, 18, 86, 89, 94, 128, 129, 436/130, 131, 132, 164, 166, 174, 147, 436/106; 252/408.1; 422/82.05, 82.09, 422/82.12

See application file for complete search history.

(56) References Cited

U.S. PATENT DOCUMENTS

| | | | | |
|---|---|---|---|---|
| 3,435,064 A | * | 3/1969 | Cinnamon et al. ............... | 560/51 |
| 3,778,230 A | * | 12/1973 | Arikawa et al. .................. | 436/43 |

(Continued)

FOREIGN PATENT DOCUMENTS

| | | |
|---|---|---|
| CN | 102618621 A | 8/2012 |
| GB | 1349491 A | 4/1974 |

(Continued)

OTHER PUBLICATIONS

Nakanishi et al. Abstract from the Japanese Journal of Dairy Science, 1971.*

(Continued)

*Primary Examiner* — Maureen Wallenhorst
(74) *Attorney, Agent, or Firm* — Jason Saunders; Arnold, Knobloch & Saunders, L.L.P.

(57) ABSTRACT

A method for analyzing one or more nitrogen-containing compounds, in which the one or more nitrogen-containing compounds are contacted with hydrindantin at an elevated temperature in a contact zone is provided. In the method ninhydrin is contacted with one or more reducing agents in a heating zone at a first elevated temperature to produce a hydrindantin-containing mixture. The hydrindantin-containing mixture is introduced into the contact zone and contacted with the nitrogen-containing compounds at a second elevated temperature. The method is particularly suitable for the analysis by visualization of amino acids.

26 Claims, 1 Drawing Sheet

(56) References Cited

U.S. PATENT DOCUMENTS 3,918,907 A     11/1975    Stephens
4,274,833 A      6/1981    Pickering

FOREIGN PATENT DOCUMENTS

SU           1597700     *   10/1990
WO     2008/081959   *    7/2008

OTHER PUBLICATIONS

Lie, S. Abstract from Mitteilungen der Versuchsstation fuer das Gaerungsgewerbe in Wien, vol. 26(9), 1972.*

Kumar, Anil, et al., $Sn^{2+}$—$Sn^{2+}$ and $Fe^{2+}$—$Fe^{3++}$ redox interaction in 30 $Na_2O$-70 $SiO_2$ glass, Department of Ceramic Engineering, Institute of Technology, Banaras Hindu University, Varanasi (India), 2096 Glastechnische Berichte 64 (1991) April, No. 4, Frankfurt, DE, 3 pages.

WPI abstract accession No. 2012N8235779, [retrieved on Oct. 3, 2013].

Notification of Transmittal of International Search Report and Written Opinion of the International Searching Authority, PCT Application No. PCT/GB2013/000507, Jan. 31, 2014, 11 pages.

Co-pending PCT Application No. PCT/GB2013/000507, Nov. 20, 2013, 41 pages.

Spackman, Darrel H.; Stein, William H. and Moore, Stanford, Automatic Recording Apparatus for Use in the Chromotography of Amino Acids, The Rockefeller Institute for Medical Research, Jul. 1958, vol. 30, No. 7, pp. 1190-1206, New York.

* cited by examiner

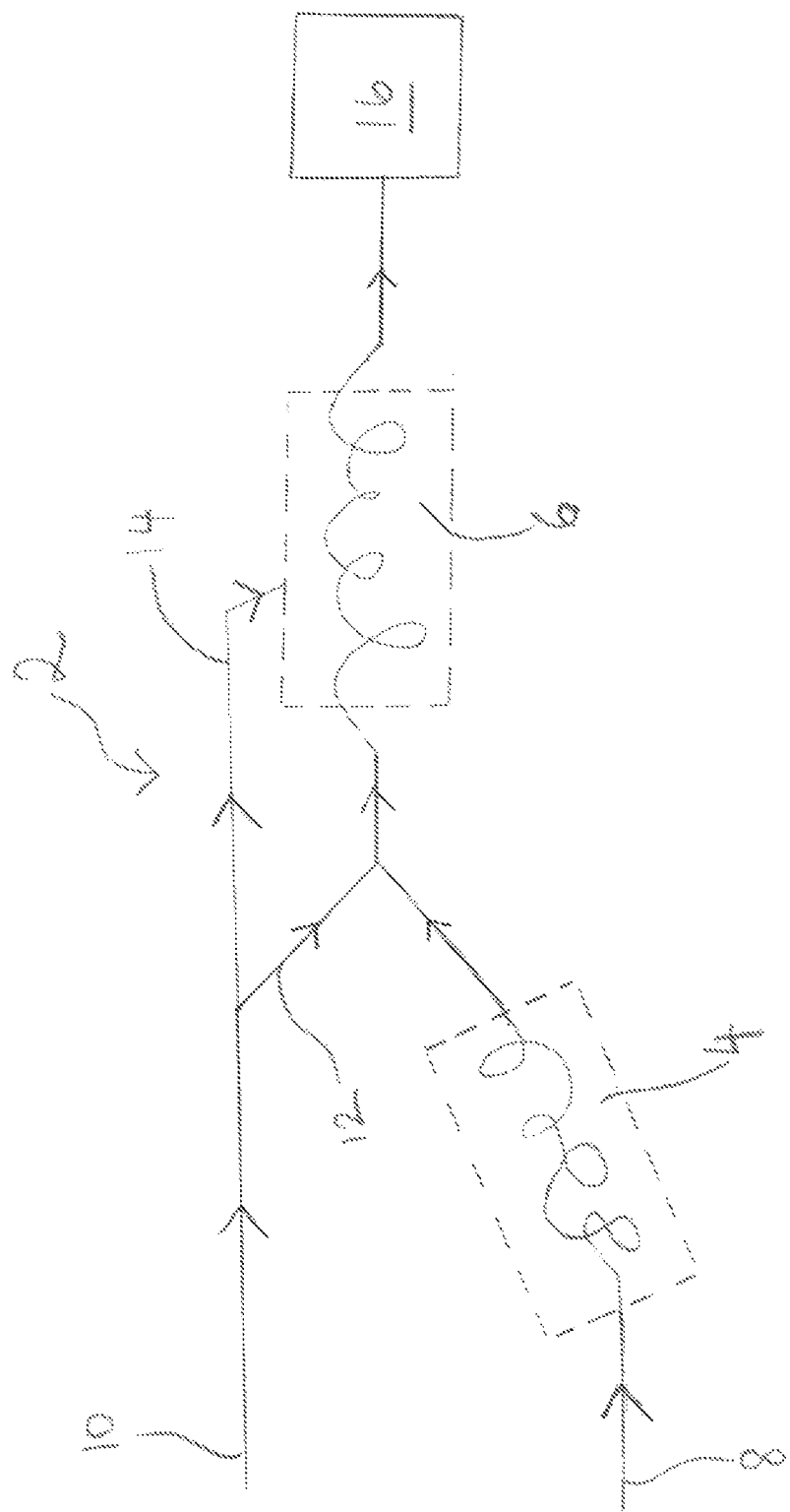

METHOD FOR ANALYSING AMINO ACIDS AND A REAGENT FOR USE WITH THE SAME

BACKGROUND OF THE INVENTION

The present invention relates to a novel method for analysing nitrogen-containing compounds, for example amino acids and the like. The present invention also provides a reagent for use in the same.

Amino acids are the components from which proteins are formed, which in turn play a key role in many biological processes. In some cases the presence or absence of a particular amino acid in an individual can seriously affect their health. For example, an individual suffering from the genetic metabolic disorder phenylketonurea cannot metabolise phenylalanine; the accumulation of which severely affects their brain development. Accordingly, methods for detecting free amino acids or determining the amino acid compositions of proteins are vital for the proper diagnosis and management of diseases. Similarly, such methods are important for the analysis of commercial drugs, food and foodstuffs, as well as protein and enzyme research and development. More generally, the detection and identification of nitrogen-containing compounds finds applications across a wide range of disciplines, including, agricultural, biochemical, clinical, environmental, food, forensic, histochemical, microbiological, medical, nutritional, plant and protein sciences.

At present, free or hydrolytically released amino acids are typically detected using automatic amino acid analysers. In the 1950's the first automated amino acid analysis method was developed by Moore, Stein and Spackman, (Spackman D H, Stein W H, and Moore S. *Automatic recording apparatus for use in the chromatography of amino acids*. Anal Chem, 1958, 30:1190-1206). This multi-stage process involves separating the amino acids by ion exchange liquid chromatography. A ninhydrin reagent is pumped from a reagent reservoir, mixed with the eluate from the ion exchange column and passed through a steel or plastic reaction coil, and heated to the temperature required for reaction.

Ninhydrin reacts with all amino acids and related amine compounds to form highly coloured reaction products. In particular, Ruhemann's purple is formed by primary amines and primary amino acids and may be measured by absorbance of light at a wavelength of 570 nm. Yellow coloured reaction products are formed by secondary amines and a number of secondary amino acids. These reaction products may be measured by its absorbance of light at a wavelength of 440 nm. The coloured reaction products vary in intensity according to the concentration of amino acid.

The amino acid reaction products are passed through a photometer where the light absorbed by the dye compounds is detected at suitable wavelengths, in particular 570 nm and 440 nm. The presence of different amino acids may be determined by chromatography. The identity of each amino acid is established on the basis of its migration characteristics and thus its position on the chromatogram. The concentration of the amino acid is determined by the intensity of the coloured product detected in the photometer by way of absorbance at the specified wavelength. Accordingly, this method may be used qualitatively and quantitatively to determine which amino acids are present in a test sample and the relative concentrations of each.

The colour reaction between ninhydrin and the amino acid or amine is very slow at room temperature. It is significantly faster at elevated temperatures, but still takes many minutes, even at a temperature of 130° C. and above. To maintain good chromatographic performance the colour reaction needs to take place in a time period of around one minute or less. To achieve this, hydrindantin, the reduced form of ninhydrin, was found to be required for the ninhydrin reagent to be effective and provide an acceptable rate of reaction. There have been a number of suggested reasons or mechanisms for explaining the ability of hydrindantin to speed up the formation of the coloured products at elevated temperatures. One suggestion is that hydrindantin acts as a stabiliser for one of the reaction intermediates. As such it is considered as an accelerator not a catalyst.

Unfortunately, hydrindantin present in the ninhydrin reagent is a very difficult compound to handle. It is particularly unstable in the presence of air, the oxygen rapidly oxidising the hydrindantin to ninhydrin. Only relatively small amounts of air are necessary to seriously deplete the hydrindantin in the reagent and thus substantially reduce the sensitivity of the colour production in the photometric analysis. An inert atmosphere, usually nitrogen, may be used both in the preparation and during the use of the ninhydrin reagent, in an attempt to reduce the oxidation of hydrindantin. As can be appreciated, the requirement for an inert atmosphere results in the need for complex equipment and handling procedures, to ensure hydrindantin, essential for rapid amino acid analysis does not deteriorate at an unacceptable rate before and/or during its use.

In addition, hydrindantin is insoluble in totally aqueous media. Accordingly a substantial amount of organic solvent is required for storage and use of the same.

In practice, using existing equipment and techniques, it is impossible to completely exclude air during mixing or use of the ninhydrin reagent comprising hydrindantin on standard amino acid analysers. As a result, the hydrindantin concentration in the reagent will inevitably steadily decrease until no colour reaction will take place in the time frame of the chromatographic analysis. In fact, a typical ninhydrin reagent comprising hydrindantin will have a shelf life of no longer than one month and maybe as short as two weeks.

Little has changed in the last 60 years since the discovery of ninhydrin based analysis requiring hydrindantin by Moore, Stein and Spackman. Rather, this method is still the most common technique used today. However, in light of the above problems associated with using hydrindantin, slight modifications to the method have been made to minimise the rate of deterioration as much as possible. The original method by Moore. Stein and Spackman employed stannous chloride as the reducing agent. However, the amount of stannous chloride required to produce sufficient hydrindantin for a reasonably fast reaction caused eventual precipitation of tin hydroxide compounds, which in turn fouled and blocked the flow tubing. The use of stannous chloride was therefore soon abandoned and other reducing agents such as cyanide, titanous salts, borohydride and ascorbic acid were investigated. Cyanide could not be used commercially because of toxicity issues and lacked the necessary stability.

More serious studies were carried out on sodium borohydride and ascorbic acid reducing agents. For example, U.S. Pat. No. 3,778,230 and U.S. Pat. No. 4,274,833 disclose ninhydrin reagents comprising ascorbic acid and sodium borohydride or stannous chloride as reducing agents respectively. However, these reagents must first be prepared in an inert container at ambient temperatures to minimise risk of oxidation of hydrindantin. With particular reference to U.S. Pat. No. 3,778,230 and the use of ascorbic acid as reducing agent, a serious disadvantage is the production of coloured by-products which adversely affect the accuracy of the results.

Alternative techniques, some using different equipment for amino acid analysis have also been proposed. For example, U.S. Pat. No. 4,359,323 relates to a liquid chromatograph analytical system for amines. The system consists of a is chromatographic column, a reaction column and a loop to recycle the mobile phase for reuse. The primary and most significant feature of this system is that the liquid mobile phase used to separate the amino acid sample is comprised of a combination of an eluent and a substance which reacts with amines to produce a compound which can be detected photometrically. Accordingly, this process only requires a single pump for complete operation. In this way, exposure of hydrindantin to the surrounding air is supposedly reduced. However, there is still a significant risk with this invention that the reactant will interfere with the amino acid sample within the separation column.

Unlike the Moore. Stein and Spackman method, Hitachi is understood to mix sodium borohydride and ninhydrin together on-line before the heated reaction chamber. Accordingly, it has been claimed that the Hitachi reagent may be used for up to a maximum of 12 months, rather than the standard 1 month of a mixed reagent. Nevertheless, sodium borohydride is still not fully stable and it is known that trace amounts of metals can accelerate its deterioration. As a result, a significant amount of the sodium borohydride could be lost before the end of one year. Although hydrindantin is produced online, an extra pumping system or line is necessary for inserting sodium borohydride into the analysis equipment. This increases the complexity and cost of the system and the Hitachi reagent will not be usable on other manufacturers' instruments, unless they are fitted with an additional pumping system and supply lines.

An alternative technique for preparing a ninhydrin reagent is disclosed in U.S. Pat. No. 3,632,496. A reagent generator is formed from an elongated housing having a channel therethrough including an inlet at one end for receiving a reagent and an outlet at the other for discharging activated reagent. The channel is defined by surfaces of metallic material catalytically active for reducing ninhydrin to form the activated reagent. In this way, ninhydrin in its stable state may be stored and activated in one vesicle. However, this invention provides an overly complicated mechanism and device for preparing activated ninhydrin reagents. As discussed above, manufacturers have since reverted to using a much simpler method, wherein ninhydrin and hydrindantin, stored separately, are mixed together immediately prior to use on the amino acid analyser. Furthermore, the reagent reactor of U.S. Pat. No. 3,632,496 is to be incorporated within a reagent sprayer, for use in applications of the field of paper chromatography. Accordingly, transferral of the activated reagent from the reagent reactor into the amino acid analyser equipment for use is likely to be difficult, if not impossible without exposing the hydrindantin to the surrounding air.

Whilst there has been considerable research into finding alternative ninhydrin reagents, in particular, alternative reducing agents, there is still a need for an improved method, providing an effective, simple and inexpensive way of analysing amino acids and the like. It would be particularly advantageous if an alternative method was available for use with a wide range of ninhydrin reagents.

SUMMARY OF EXAMPLES OF THE INVENTION

Accordingly, in a first aspect, the present invention provides a method for analysing one or more nitrogen-containing compounds, in which the one or more nitrogen-containing compounds are contacted with hydrindantin at an elevated temperature in a contact zone, the method further comprising:

contacting ninhydrin with one or more reducing agents in a heating zone at a first elevated temperature to produce a hydrindantin-containing mixture; and introducing the hydrindantin-containing mixture into the contact zone and contacting the hydrindantin-containing mixture with the nitrogen-containing compounds at a second elevated temperature.

The method of the present invention may be used for visualising nitrogen containing compounds, more particularly for quantitatively and qualitatively analysing amino acids and amines. The method is based on the well-established amino acid and ninhydrin reaction used in commercially available amino acid analysers. As discussed above, commercially available systems typically separate a test sample into its amino acid constituents by ion exchange liquid chromatography. The eluted amino acids are then mixed with a ninhydrin reagent comprising hydrindantin and heated within the reaction coil to form coloured reaction products which are subjected to photometry in known manner.

Ninhydrin is known in the art and is commercially available. The ninhydrin reagent used in the method of the present invention may comprise reducing agents known in the art for the reduction of ninhydrin and in the analysis of amino acids. More preferably however, the ninhydrin reagent comprises one or more compounds referred to herein as 'temperature-dependent reducing agents'. A more detailed explanation of the temperature-dependent reducing agents suited for use in this method and the tests for assessing their suitability is provided below in the second aspect of the present invention. The following description refers to the ninhydrin reagent comprising one or more temperature-dependent reducing agents. However, it is to be understood that the method of the present invention may also be applied to ninhydrin reagents comprising other reducing agents, as may be known in the art.

As discussed above, in the method of the present invention, ninhydrin is contacted with one or more reducing agents at a first elevated temperature to produce a hydrindantin-containing mixture, prior to being introduced into the contact zone at a second elevated temperature for reaction with the nitrogen-containing compounds being analysed. Ever since Moore, Stein and Spackman's chromatographic method was developed for the determination of amino acid and related amines, all instrumental developments involve only one heating stage within the contact zone or reaction coil. It has been found that pre-heating ninhydrin and the one or more temperature-dependent reducing agents in this manner improves the reactivity of the reducing agents, in turn improving the overall operation and efficiency of the analytical method. Perhaps more importantly, it has been found that the increase in heating time does not affect the chromatographic performance of amino acid analyser instruments. In fact, pre-heating ninhydrin and the one or more temperature-dependent reducing agents has been found to increase substantially the sensitivity of the subsequent amino acid analysis. Yet still further, applying a pre-heating stage has been found to increase the number of compounds and compound types capable of use as temperature-dependent reducing agents in the reduction of ninhydrin to hydrindantin as will be discussed in more detail below.

The method of the present invention uses a heating zone, such as a pre-heating coil or column, for pre-heating the one or more temperature-dependent reducing agents to the first elevated temperature prior to the reagents being provided to the contact zone. The heating zone, such as the pre-heating coil or column, is used to preheat the temperature-dependent reducing agent and ninhydrin to form hydrindantin in the absence of the nitrogen-containing compounds and prior to contact with the nitrogen-containing compounds being analysed in the contact zone.

The heating zone and the contact zone may be within a single chamber or vessel or may be housed within separate vessels.

In one embodiment, the heating zone and the contact zone are contained within the same heating chamber, the heating zone being located upstream of the contact zone. In this arrangement, the heating zone and the contact zone may be exposed to the same temperature or to a different temperature. Further, the heating zone and contact zone may be operated to heat the ninhydrin reagent and/or nitrogen containing compounds for the same or different amount of time. In this embodiment, it is more convenient to have the single heating chamber operating at a single temperature, such that the heating zone and the contact zone are at the same temperature.

Alternatively, the heating zone is contained within a separate chamber or vessel to that of the contact zone and located upstream of the contact zone. In this embodiment, the heating zone and the contact zone may be operated at the same or different temperatures. Further, the heating zone and contact zone may be operated to heat the ninhydrin reagent and/or nitrogen containing compounds for the same or different amount of time. Arranging the contact zone and heating zone so that the temperature and reaction time in each may be varied and controlled independently offers much more versatility in terms of controlling the formation of hydrindantin during use. This is in contrast to known methods, in which the concentration of the reducing agent is fixed and wherein the rate at which hydrindantin is formed cannot therefore be controlled.

This arrangement of using a pre-heater to pre-heat the ninhydrin reagent is particularly advantageous for developing an organic solvent free reagent as the reagent components will generally be more soluble at higher temperatures. In addition, compounds with a relatively low reducing activity, such as the temperature-dependent reducing agents of the present invention, may be subjected to additional heating in order to render them sufficiently active to reduce ninhydrin to hydrindantin. Accordingly, the method of this aspect of the present invention provides for the use of a wider range of components as reducing agents for ninhydrin.

The contact zone is used to contact the activated ninhydrin reagent, that is, the reagent containing hydrindantin, with the nitrogen-containing compounds, such as one or more amino acids, to the second temperature. Hydrindantin production by the reduction of ninhydrin continues in the contact zone, that is, the colour forming reaction coil of the apparatus. However, by controlling the concentration of the temperature-dependent reducing agent, the temperature within the contact zone and the reaction time, the concentration of hydrindantin is allowed to increase at a controllable rate. More significantly, as noted above, the temperature within the contact zone is not constrained by the need to form hydrindantin in the required concentration, this having been achieved in the heating zone. In this way, the conditions in the contact zone can be optimised for analysis of the nitrogen-containing compounds, in particular the colour forming reactions with amino acids.

The contact zone may be of any suitable configuration to allow the activated ninhydrin reagent containing hydrindantin to contact the nitrogen-containing compounds being analysed. Preferably the contact zone is configured in a similar manner to the heating zone of the present invention, that is, in the form of a coil or column.

Ninhydrin and the one or more temperature-dependent reducing agents of the method of this aspect of the present invention may be delivered to the heating zone separately. For example, ninhydrin and the one or more reducing agents may be drawn from separate containers or reservoirs by respective pumps and delivered to a common line or mixing zone, where they are combined to form a mixture. This mixture is then delivered to the heating zone. Alternatively, ninhydrin and the one or more reducing agents are drawn from separate containers or reservoirs by respective pumps and delivered to the heating zone directly, where they are both mixed and heated.

More preferably however, ninhydrin and the one or more temperature-dependent reducing agents are delivered to the heating zone together as a mixture as it is more convenient to prepare the components of the mixture prior to their use on the amino acid analysis equipment. Further, by using the temperature dependent reducing agents of the present invention, the components of the mixture are very stable and the mixture may be prepared in advance of actually being used and have a long shelf life in the presence of air.

As discussed above, commercially available ninhydrin reagents are prepared by combining solutions of ninhydrin with hydrindantin. In addition, ninhydrin reagents typically comprise one or more buffers and organic solvents. Accordingly, in a preferred embodiment, a hydrindantin free ninhydrin reagent, comprising ninhydrin, one or more temperature-dependant reducing agents one or more buffers and one or more organic solvents, are contacted at the first temperature in the heating zone.

The components of the ninhydrin reagent, that is ninhydrin, the temperature-dependent reducing agent and one or more buffers and/or solvents, may be provided to the heating zone in the many ways described above, that is separately or with one or more components combined. More preferably however, components of the ninhydrin reagent are delivered to the heating zone together as a mixture, as it is more convenient to prepare the components of the mixture prior to their use in the analysis.

As discussed above, advantageously, the method of the present invention does not necessarily require the presence of a separate organic solvent, as is the case with known methods and ninhydrin reagents. However, it has been found that many organic solvents, when used according to the method of the present invention are capable of acting as temperature-dependent reducing agents. Accordingly an alternative embodiment the ninhydrin reagent used in the method of the present invention comprises one or more organic solvents as temperature-dependent reducing agents. In this embodiment, the organic solvent may be the sole temperature-reducing agent. Alternatively, the ninhydrin reagent may comprise one or more additional temperature-dependent reducing agents. In this embodiment, the ninhydrin, organic solvent, optional one or more temperature dependent reducing agents and requisite buffer(s) may be introduced in any one of the ways mentioned above.

More detailed information regarding the type of buffers and solvents suitable for forming part of the ninhydrin reagent for use in the method of the present invention is provided below.

The temperature at which ninhydrin and the temperature-dependent reducing agent react to produce hydrindantin will vary according to the dwell time in the heating and contact zones at the respective first and second temperatures. In addition, the dwell time of the coils will vary with the flow rate chosen for the chromatography, which can vary depending on type of nitrogen-containing sample, in particular amino acid sample being analysed. Further the exact composition of the reagent, for example, the concentration and reducing strength of the temperature-dependent reducing agent and the amount of organic solvent present will determine the temperature setting within the heating and contact zones.

In light of the above, ninhydrin and the temperature-dependent reducing agent may be contacted in the heating zone at a first temperature in the range of from 100° C. to 160° C., more preferably from 115° C. to 145° C., still more preferably from 120° C. to 135° C.

Further, the ninhydrin and the temperature-dependent reducing agent may be contacted in the heating zone for any suitable length of time, in particular a period sufficient to produce the required concentration of hydrindantin. The dwell time in the heating zone will depend upon such factors as the concentration of the temperature-dependent reducing agent, the activity of the reducing agent, the first temperature being applied and the concentration of hydrindantin required. In particular, the dwell time in the heating zone may vary from 10 to 180 seconds, preferably from 15 to 120 seconds, more preferably from 20 to 80 seconds, still more preferably from 30 to 60 seconds.

As discussed above, the components of the ninhydrin reagent are contacted in the heating zone at the first temperature to produce an activated hydrindantin-containing mixture. The hydrindantin-containing mixture is then delivered from the heating zone to the contact zone. The contact zone is where the reagent is contacted with the nitrogen-containing compounds being analysed and the colour forming reaction takes place between the ninhydrin reagent and the nitrogen-containing compounds, such as one or more amino acids.

The production of hydrindantin prior to the ninhydrin reagent being introduced to the contact zone results in faster colour-producing reactions in the contact zone, in turn allowing shorter dwell times to be employed, with substantially increased sensitivity. Further, the production of hydrindantin prior to the ninhydrin reagent being introduced to the colour forming contact zone means that higher sensitivities are possible for ninhydrin reagents containing no organic solvents.

As noted above, the hydrindantin-containing mixture leaving the heating zone is contacted with nitrogen-containing compounds in the contact zone. The nitrogen-containing compounds, such as one or more amino acids, may be introduced into the system at any convenient point in the procedure, provided this is downstream of the heating zone. For example, the amino acids may be drawn from the ion exchange column to a location downstream of the heating zone but upstream of the contact zone and mixed with the hydrindantin-containing mixture. This mixture is then directed to the contact zone. In an alternative arrangement, the amino acids are drawn from the ion exchange column directly into the contact zone to mix therein with the activated hydrindantin-containing mixture.

The hydrindantin-containing mixture leaving the heating zone is contacted with the nitrogen-containing compounds in the contact zone, at the second temperature as discussed above. Similarly, the second temperature within the contact zone may be varied according to such factors as the concentration and activity of the temperature-dependent reducing agent used in the method of the present invention, the dwell time in the contact zone, and the nature of the nitrogen-containing compounds, in particular in order to optimise the colour-forming reactions in the contact zone. Preferably the second temperature is in the range of from 100° C. to 160° C., still more preferably from 115° C. to 145° C., more preferably still from 120° C. to 135° C.

The residence or dwell time of the components in the contact zone may similarly vary according to the aforementioned factors, including the temperature of the contact zone. Preferably, the dwell time in the contact zone is in the range of from 10 to 100 seconds, more preferably from 20 to 80 seconds, still more preferably from 30 to 60 seconds.

The ability to independently control the dwell times and temperatures of the two heating stages provides improved control of hydrindantin production and its use in the colour forming reaction. In particular, much higher concentrations of hydrindantin can be generated producing faster colour formation with significantly reduced or no danger of precipitation of components in the contact zone.

As discussed above, any temperature-dependent reducing agent may be used in the method of the present invention. More preferably however, the ninhydrin reagent according to the second aspect of the present invention is used. As mentioned above, it is particularly advantageous to use a so-called temperature dependent reducing agent in the reduction of ninhydrin in the heating zone.

Accordingly, in a second aspect the present invention provides a ninhydrin reagent for use in a method for analysing nitrogen-containing compounds, in particular amino acids and the like, wherein the ninhydrin reagent comprises;
ninhydrin;
an aqueous buffer; and
a temperature-dependent reducing agent, which agent is inactive in the reduction of ninhydrin at a lower temperature and active in reducing ninhydrin to hydrindantin at a higher temperature than the lower temperature.

The present invention further provides a method of analysing a nitrogen-containing compound using the aforementioned ninhydrin reagent, in which ninhydrin is contacted with the reducing agent in the form of a ninhydrin reagent in the heating zone, the ninhydrin reagent comprising:
ninhydrin;
an aqueous buffer; and
a temperature-dependent reducing agent, which agent is inactive in the reduction of ninhydrin at a first temperature and active in reducing ninhydrin to hydrindantin at a second temperature, wherein the second temperature is higher than the first temperature;
the ninhydrin reagent being heated to at least the second temperature in the heating zone.

A compound is deemed to be a temperature-dependent reducing agent if it is inactive in the reduction of ninhydrin at a first, lower temperature and active in reducing ninhydrin to hydrindantin at a second, higher temperature. In this respect, the term 'inactive' when used in relation to the reduction of ninhydrin at the lower temperature is a reference to the compound having an activity at or below a maximum activity. Similarly, the term 'active' when used in relation to the reduction of ninhydrin at the higher temperature is a reference to the compound having an activity at or exceeding a minimum activity, as discussed in more detail below.

Compounds for use in forming the temperature-dependent reducing agent of the ninhydrin reagent may have a reducing activity capable of reducing ninhydrin at a rate comparable to those of known reducing agents. However, it is preferred that the temperature-dependent reducing agent of the ninhydrin reagent is less active and reduces ninhydrin at a lower rate than those reducing agents employed commercially. This has the advantage of easier control of the reduction reaction.

To be suitable for use as a temperature dependent reducing agent in the present invention, a given compound must be active in the reduction of ninhydrin and exhibit a minimum activity at the higher temperature. In order to assess whether a particular compound has sufficient activity in the reduction of ninhydrin at the higher temperature. Protocol 1 was devised; details of which are provided in Example 1. Compounds meeting the requirements of Protocol 1 are considered to have at least a minimum activity in the reduction of ninhydrin to hydrindantin at a higher or threshold temperature.

According to the method of the Protocol 1, a compound is considered sufficiently active in reducing ninhydrin if at a threshold temperature, that is the aforementioned higher temperature, it has a minimum degree of activity, that is, is able to reduce a given amount of ninhydrin in a specified period of time. In this protocol, the threshold temperature is 100° C.

According to Protocol 1, ninhydrin and an amino acid solution, namely, glycine, is mixed with a solution of the selected compound at a threshold temperature of 100° C. After 35 minutes, the intensity of Ruhemann's purple produced, if any, is calculated by measuring the absorption of the solution using a standard spectrophotometer at a specified wavelength of 570 nm. A strong intensity of colouration indicates that the selected compound has a high degree of activity at the threshold temperature. More preferably, for the purposes of assessing whether the selected compound has the minimum degree of activity required for forming part of the ninhydrin reagent of the present invention, a minimum absorbance of 0.2 is required. The minimum activity of the compound in the reduction of ninhydrin at the second temperature is one that provides an absorbance of at least 0.2 in the aforementioned test. An absorbance below about 0.2 indicates that the compound is not sufficiently active at the higher temperature in the reduction of ninhydrin for use in the ninhydrin reagent of the present invention. More preferably, the minimum absorbance to be achieved by the candidate compound is at least 0.3.

In addition to the above, compounds for use in forming the temperature-dependent reducing agent in the ninhydrin reagent of the present invention must be inactive in the reduction of ninhydrin at a first, lower temperature.

The lower temperature at which the compounds are required to be inactive is lower than the aforementioned threshold temperature. Typically, the lower temperature is a temperature or range of temperatures at which the reagent is typically stored and/or transported, prior to use in an analyser or for the purposes of visualising nitrogen containing compounds in general. Existing ninhydrin reagents are typically stored at room temperature or below. Accordingly, the lower temperature is preferably room temperature. As room temperature typically varies due to external actors, the first temperature is preferably up to 30° C., still more preferably up to 25° C., more preferably still at or below 20° C. The first temperature is preferably greater than 0° C., still more preferably greater than 5° C., more preferably still greater than 10° C. In one embodiment, the first temperature is from 5° C. to 25° C. Yet still more preferably the first temperature is from 10° C. to 20° C.

The compounds identified as being inactive at the lower temperature include compounds which are not normally considered to have any significant reducing action at the said lower temperature, but which become sufficiently strong reducing agents at the aforementioned higher, threshold temperature, reacting with ninhydrin to form hydrindantin. In addition, the temperature-dependent reducing agents identified as being inactive at the lower temperature include compounds known to have only weak reducing activity (that is below the maximum activity defined above) at the lower temperature, but which become sufficiently strong reducing agents at the higher, threshold temperature, reacting with ninhydrin to form hydrindantin.

In order to determine whether a compound is sufficiently inactive at the lower temperature. Protocol 2 has been devised; details of which are provided in Example 2. Protocol 2 may be performed prior to or after the Protocol 1 provided in Example 1. More preferably, Protocol 2 is performed after Protocol 1 has been used to establish that the selected compound has the minimum degree of activity required at the threshold or higher temperature for the reduction of ninhydrin.

According to the method of Protocol 2, a ninhydrin reagent comprising the selected compound is prepared and stored at the lower temperature in the presence of air. At set time intervals, a sample is taken from the ninhydrin reagent, mixed with an amino acid solution of glycine and heated to the aforementioned higher, threshold temperature. For the purposes of continuity with respect to Protocol 1 provided in Example 1, the higher temperature is preferably 100° C., as discussed above. The intensity of Ruhemann's purple produced, if any, is calculated by measuring the absorbance of the solution at 570 nm using a standard spectrophotometer. Measuring the intensity over successive samples, in particular determining the rate of any decrease in intensity of coloration, indicates whether the long term stability of the selected compound is suitable for the compound to be used in the ninhydrin reagent of the present invention.

According to Protocol 2 a selected compound is deemed not to be sufficiently stable at the lower temperature and therefore not suitable for use as a temperature dependent reducing agent in the ninhydrin reagent of the present invention, if the corrected absorbance drops to less than 50% after 1 month. That is, compounds suitable for use in forming the temperature-dependent reducing agent in the ninhydrin reagent of the present invention have an activity of at least 50% of their initial activity after 1 month. More preferably, the selected compound is considered suitable for use in the ninhydrin reagent of the present invention, if the corrected absorbance is no less than 50% after 3 months, still more preferably if the corrected absorbance is no less than 50% after 6 months. Particularly preferred compounds are those in which the corrected absorbance in the batch stability test is at least 50% after 12 months, still more preferably if the corrected absorbance is at least 50% of the initial absorbance after 24 months.

It has been found that compounds having the properties set out above and able to meet the requirements of the Protocol 1 of Example 1 and meet or exceed the requirements of Protocol 2 of Example 2 are most advantageous for use in a ninhydrin reagent. As noted above, using the methods provided in both Examples 1 and 2, a range of compounds have been found to be sufficiently stable at the first, lower temperature whilst also having the minimum degree of activity required at the second, higher temperature for use in the ninhydrin reagent of the present invention. While these compounds may vary according to their degree of activity at the higher temperature, they all have the minimum degree of activity required for use in the ninhydrin reagent of the present invention.

As indicated, Protocol 1 of Example 1 and Protocol 2 of Example 2 have been used to screen a range of compounds for their suitability for use as the temperature-dependent reducing agent of the ninhydrin reagent of the present invention. The ninhydrin reagent may comprise a single temperature-dependent reducing agent. Alternatively, the reagent may comprise a combination of two or more temperature-dependent reducing agents.

Suitable compounds for use as the temperature-dependent reducing agent of the ninhydrin reagent of the present invention are known in the art and are commercially available In one embodiment, the temperature-dependent reducing agent comprises one or more saccharides. Many saccharides have mild reducing properties and are sometimes called reducing sugars. A reducing sugar can be defined as one containing a hemiacetal or hemiketal group in its cyclic form producing an aldehyde or ketone group in its open ring form. All monosaccharides and many disaccharides are reducing sugars.

Preferred monosaccharide's include glucose and fructose, which in their cyclic forms have an hemiacetal and a hemiketal group respectively. Glucose and fructose were both found to have sufficient reducing activity at the higher, threshold temperature whilst remaining stable at the lower temperature in the presence of air, when subjected to the aforementioned Protocol 1 and Protocol 2.

Fructose was found to have a shelf life of approximately 3 years at room temperature. Although not as reactive in the reduction of ninhydrin at the higher temperature, glucose was found to be more stable than fructose, having a shelf life of longer than 4 years at room temperature. Accordingly, if a longer shelf life is required, the ninhydrin reagent of the present invention preferably comprises glucose.

Other monosaccharides suitable for use as temperature-dependent reducing agents include aldose compounds such as Glyceraldehyde, Galactose, Ribose, Xylose, Erythrose, Threose, Lyxose, Arabinose, Allose, Altrose, Mannose, Gulose, Idose, Talose and L-Glycero-D-manno-heptose and ketose compounds such as Dihydroxyacetone, Erythrulose, Ribulose, Xylulose, Psicose, Sorbose, Tagatose and Sedoheptalose.

In general, disaccharides and polysaccharides will not have the properties required to form suitable temperature-dependent reducing agents when used in a standard amino acid analyser. However, when used according to the method of the first aspect of the present invention, sucrose, a non-reducing disaccharide, was found to be sufficiently active in the reduction of ninhydrin to hydrindantin when assessed according to the test protocol. Like sucrose most other non-reducing sugars will also now be sufficiently active to reduce ninhydrin to hydrindantin. In general these very weak temperature dependent reducing agents will require higher concentrations to pass Protocol 1 described in Example 1.

There are a significant number of disaccharides and polysaccharides comprising a hemiacetal or hemiketal group in their cyclic form. These types of saccharides have been found particularly capable of acting as temperature-dependent reducing agents as defined by Protocol 1 and Protocol 2. The disaccharides, lactose and maltose are two such examples.

A non-exhaustive list of other disaccharides capable of acting as temperature dependant reducing agents in the method of the present invention include Trihalose, Cellobiose, Kojibiose, Nigerose, Isomaltose, Sophorose, Laminaribiose, Gentiobiose, Turanose, Maltulose, Palatinose, Gentiobiulose, Mannobiose, Melibiose, Melibiulose, Rutinose and Xylobiose.

Even longer chain polysaccharides can be reducing sugars. The tetrasaccharose, Stachyose, is an example. Much longer chain polysaccharides such as starch have too few reducing units to be suitable, but partially hydrolysed starch such as the dextrins and maltodextrins have significant reducing action. However, these long chain polysaccharides can give more viscous solutions and possible precipitation problems.

In an alternative embodiment, the temperature-dependent reducing agent may comprise one or more carboxylic acids and/or their salts. In general, simple monofunctional carboxylic acids, comprising only a single carboxylic acid group and no other functional group, have not been found capable of acting as temperature-dependent reducing agents according to Protocol 1 and Protocol 2. Such monofunctional carboxylic acids include acetic, propionic, and benzoic acid. However, formic acid and its salts have been found to be capable of acting as temperature-dependent reducing agents according to the aforementioned Protocol 1 and Protocol 2.

Suitable salts of carboxylic acids for use in the temperature-dependent reducing agent include metal salts, in particular Group I and Group II metal salts, for example potassium, sodium, calcium and magnesium salts.

Sodium formate, the sodium salt of formic acid, has been found to be sufficiently inactive in the reduction of ninhydrin at a first, lower temperature and active in reducing ninhydrin to hydrindantin at a second, higher temperature, according to Protocol 2 and Protocol 1 respectively. In particular, sodium formate was found to have a reducing activity between that of glucose and fructose. Further, the shelf life was similar to that of glucose having a shelf life in excess of 4 years.

Other carboxylic acids and/or their salts suitable for use as temperature-dependent reducing agents according to the present invention are those comprising at least one additional reducing group, for example one or more of a hydroxyl, ketone or aldehyde group. Citric acid, a hydroxy carboxylic acid for example, was found to act as a temperature dependent reducing agent under the conditions of the present invention. Other hydroxy carboxylic acids such as tartaric acid were found to act in the same way.

Preferred carboxylic acids have from 1 to 24 carbon atoms, more preferably 1 to 18 carbon atoms, still more preferably from 1 to 12 with $C_1$ to $C_6$ aldehydes and ketones being especially preferred. The compounds may be straight chained, branched or cyclic.

Other compounds comprising aldehyde and ketone groups, with or without the presence of hydroxyl groups, (including the simple aldehydes and ketones themselves) have been found to meet the requirements of Protocol 1 and Protocol 2. Preferred compounds of this type have from 1 to 24 carbon atoms, more preferably 1 to 18 carbon atoms, still more preferably from 1 to 12 with $C_1$ to $C_6$ aldehydes and ketones being especially preferred. The compounds may be straight chained, branched or cyclic. Examples of suitable aldehydes and ketones include acetone.

Similarly, alcohols containing one or more hydroxyl groups have been found suitable for forming the temperature-dependent reducing agent of the present invention. Preferred alcohols have from 1 to 12 carbon atoms, more preferably from 1 to 8, still more preferably from 1 to 6 carbon atoms, with $C_1$ to $C_4$ alcohols being especially preferred. The alcohols may be straight chained or branched. Monohydric alcohols suitable for use include methanol, ethanol and propanol. Suitable polyhydric alcohols include polyethylene glycol, ethylene glycol, propylene glycol, mannitol and sorbitol. Ethylene glycol has been found to have a relatively low degree of activity in the reduction of ninhydrin when used according to the present invention and therefore needs to be present at relatively high concentrations. However, it was found to be highly stable in the presence of air; having a shelf life of longer than 4 years.

Further, it is an advantage that ethylene glycol may function both as an organic solvent and as a reducing agent. It will be noted that a number of the above compounds are already being used as organic solvents in ninhydrin reagents for the sole purpose of maintaining the solubility of hydrindantin and preventing precipitation either during storage or during analysis. It emphasizes the novelty of this present invention whereby a two stage heating system can now allow the use of these organic solvents for both solubility and the production of hydrindantin at high temperature.

Other organic solvents containing hydroxyl and ether groups are suitable for forming the temperature-dependent reducing agent of the present invention. Preferred compounds have from 1 to 12 carbon atoms, more preferably from 1 to 8, still more preferably from 1 to 6 carbon atoms, with $C_1$ to $C_4$ compounds being especially preferred. Examples of suitable compounds are methoxy ethanol, propylene glycol monomethyl ether and carbitol. Yet still further, organic solvents containing sulphur in low oxidation states, such as dimethylsulfoxide and sulfolane may be used as the temperature-dependent reducing agent of the ninhydrin reagent The temperature-dependent reducing agent used in the method of the present invention may also comprise one or more inorganic compounds, provided they too meet the requirements of Protocol 1 and Protocol 2. In particular, inorganic compounds comprising sulphur in low oxidation states such as sulfites and thiosulfates and/or inorganic compounds comprising phosphorus oxyacids in low oxidation states such as phosphites and hypophosphites may be particularly suitable. For example, it has been found that phosphorous acid, including its phosphite salts such as lithium, sodium and potassium, passes both Protocol 1 and Protocol 2 with an activity between that of fructose and sodium formate.

The temperature-dependent reducing agents for use in the ninhydrin reagent of the present invention are generally known in the art and are either commercially available or may be prepared in a manner analogous to known synthesis routes.

It is to be appreciated that other compounds or classes of compounds which have not been identified above may be suitable components for use as the temperature-dependent reducing agent of the ninhydrin reagent of the present invention, on condition that they meet the requirements of both Protocol 1 and Protocol 2. In general, in addition to meeting the requirements of Protocol 1 and Protocol 2, the temperature-dependent reducing agent should be readily soluble in or miscible with water and not cause precipitation when combined with other components of the reagent and/or the components used or produced in the analysis methods. It is also advantageous that the temperature-dependent reducing agent is substantially non-toxic.

In light of the above the ninhydrin reagent may comprise the temperature-dependent reducing agent in any suitable concentration. This will vary according to the temperature-dependent reducing agent employed, in particular according to such factors as the degree of activity at the higher temperature. The concentration of the temperature-dependent reducing agents may be in the range of from 0.01% to 75% w/v or v/v. More preferably, the concentration of the temperature-dependent reducing agents is from 0.01% to 20% w/v or v/v. It has been found that at concentrations higher than 20% w/v or v/v, components of the reagent may be more likely to precipitate out of solution or cause other components to precipitate out of solution and accordingly concentrations below 20% are to be preferred.

Advantageously, the heating zone used in the method of the present invention enables the use of a wide range of compounds as temperature-dependent reducing agents. These compounds can differ quite significantly in terms of their composition and reducing activity. Surprisingly, compounds with very weak reducing activity have been found to be particularly suited to use as temperature-dependent reducing agents in the method of the present invention.

In general the most active temperature-dependent reducing agents such as the reducing sugars, formic acid and phosphorous acid will require concentrations from 0.01 to 5% w/v or v/v. The intermediate active compounds such as non-reducing sugars and citric acid require concentrations from 5 to 20% w/v or v/v. Finally, the weakest compounds such as the organic solvents methanol and ethylene glycol, require concentrations from 20 to 75% v/v. In all cases, it is to be borne in mind that too high a concentration of the compound under investigation may cause components to precipitate out of solution. Alternatively or in addition, this may cause some other adverse effect leading to inaccurate measurements.

When preparing the ninhydrin reagent for use in an analytical method, the starting concentration of the temperature-dependent reducing agent is preferably similar to that which was identified in Protocol 1 provided according to Example 1, as responsible for providing an actual absorbance of at least 0.2, more preferably an absorbance from 0.2 to 0.7. More preferably, as a result of repeating Protocol 1 according to Example 1 several times, each time increasing the percentage concentration of the temperature-dependent reducing agent, the concentration which provides the highest absorbance between 0.6 and 0.7 without precipitating out of solution or adversely affecting the other components of the ninhydrin reagent is used as the starting concentration.

The ninhydrin reagent of the present invention further comprises ninhydrin and an aqueous buffer. Ninhydrin and suitable aqueous buffers are both commercially available and known for use in existing ninhydrin reagents.

The ninhydrin reagent of the present invention may comprise ninhydrin in any suitable amount. Preferably, the concentration of ninhydrin in the reagent is from 0.5 to 3% w/v. More preferably, the concentration of ninhydrin is from 1 to 2.5% w/v. Yet still more preferably, and as per Protocol 1 according to Example 1, the concentration of ninhydrin in the reagent is about 2% w/v.

Any suitable aqueous buffer may be used in the ninhydrin reagent. Suitable buffers are known in the art. An acidic buffer is preferred. More preferably, a weak acidic buffer is preferred so as to maintain the pH at a value of between 3 to 7, more preferably from 4 to 6, still more preferably from 4.5 to 5.5. A particularly suitable pH is between 5.2 and 5.3.

The buffer may be prepared from any weak acid and one of its conjugate bases/salts. The acid may be an organic acid or an inorganic acid. Organic acids are preferred, examples of which include acetic acid, ethanoic acid and propanoic acid. One preferred combination is acetic acid and one of its salts. The acid salt may be any suitable salt. The salt may be formed from any metal cation. However it is preferable that the salt is formed from any one of the alkali metals, in particular lithium, sodium or potassium.

As noted above, hydrindantin is insoluble in a totally aqueous media. In light of this, commercially available ninhydrin reagents, comprising hydrindantin, cannot be manufactured or used without the presence of a substantial amount of organic solvent. It is an advantage of the present invention however, that the ninhydrin reagent of the second aspect of the invention, when used in the method of the first aspect of the present invention, need not comprise an organic solvent or mixture of organic solvents. This is due to the fact that the temperature-dependent reducing agents are soluble in aqueous solutions and the fact that a pre-heater is used. The use of a pre-heater allows the production of lower levels of hydrindantin while still maintaining high sensitivity and as such the possibility of precipitation is very small. As a consequence, the manufacturing costs are reduced, the reagent is less harmful to the environment and waste disposal procedures are simplified.

The presence of an organic solvent in the ninhydrin reagent may affect the efficacy of the reagent. However, the sensitivity of the reagent of some embodiments of the present invention that do not comprise an organic solvent has been found to be only approximately 10% lower than that of commercially available reagents which comprise an organic solvent or mixture of organic solvents. In addition, in the absence of organic solvents and with a pre-heater, the risk of precipitation will be much lower.

Notwithstanding the above, the reagent of the present invention, when formulated without an organic solvent, provides at least acceptable results when used for amino acid analysis. In addition, optimisation of the concentration of the temperature-dependent reducing agent according to Protocol 1 and Protocol 2 will further minimise the risk of precipitation.

In an alternative and preferred embodiment, the ninhydrin reagent of the present invention further comprises an organic solvent or mixture of organic solvents. Organic solvents typically used in commercially available reagents include, dimethylsulfoxide, ethylene glycol, propylene glycol, sulfolane, hydroxy ethers such as carbitol, propylene glycol monomethyl ether and methylcellosolve and simple alcohols such as methanol, either alone or as mixtures. The addition of an organic solvent will increase the sensitivity of the ninhydrin reagent of the present invention. This should be taken into account when using the preferred ninhydrin reagent on a chromatographic system, as is discussed in more detail below.

The total concentration of organic solvent used will vary according to the nature of the organic solvent. In particular, the total concentration of organic solvent used will vary from 10% v/v to 75% v/v. More preferably, the total concentration of organic solvent used will vary from 25% v/v to 65% v/v. Yet still more preferably, the total concentration of organic solvent used will vary from 35% v/v to 55% v/v. Whilst any of the above commercially available organic solvents may be used, in accordance with the chromatography examples shown below, the method of the present invention preferably employs 40% v/v to 55% v/v ethylene glycol.

It is known in the art to include one or more organic solvents in ninhydrin reagents. It has now been found that compounds previously used and known for use as solvents in ninhydrin reagents are active as temperature dependent reducing agents when used according to the method of the first aspect of the present invention. For example, ethylene glycol, known and commercially used as a solvent for ninhydrin, has now been found to be active as a temperature-dependent reducing agent when used in the method of the present invention.

Accordingly, in a further aspect, the present invention provides the use of a temperature-dependent reducing agent, as hereinbefore defined, for reducing ninhydrin to hydrindantin in the method of the first aspect of the present invention. In particular, the temperature-dependent reducing agent comprises one or more of the aforementioned organic solvents.

As noted above, a range of temperature-dependent reducing agents have been identified using Protocol 1 and Protocol 2, as being inactive at a first temperature and active at a second threshold temperature to reduce ninhydrin to hydrindantin. Protocol 1, Protocol 2 and embodiments of the present invention will now be described in the following examples.

EXAMPLES

Example 1

Protocol 1

Protocol 1 of the present invention is comprised of the following steps;
1) Prepare the Following Solutions:
i) A 1M lithium, sodium or potassium acetate/acetic acid aqueous buffer at between pH 5.2 and 5.3, containing 2% ninhydrin w/v and a chosen starting concentration (w/v or v/v) of compound X. It is preferred to start with 0.01% w/v or v/v and gradually increase the concentration in stages. High concentrations of water soluble solids or liquids, particularly approaching 50% and above may be difficult to evaluate, due to solubility problems or other adverse effects after preparation or when used on an analytical system.
ii) A standard solution of glycine at a concentration of 1.0 mM in pure water. As previously discussed, glycine is chosen as the standard reference amino acid.
2) In a glass test tube measuring close to 15 cm long and 1.5 cm in outside diameter, add 2.0 ml of solution of i) above, 0.20 ml of the standard glycine solution ii) and 2.8 ml of pure water.
3) Place the test tube into a liquid heating bath at 100° C. and leave undisturbed for 35 minutes. Take out the test tube and cool quickly to room temperature.
4) Transfer the cooled solution into a 1 cm cuvette and measure the absorbance at 570 nm against pure water using a standard spectrophotometer or colorimeter.
5) At the same time as the compound is being assessed for activity, a blank sample should also be performed in case there are amino acid or amine impurities in the reagents. The procedure is the same as in 2) above except that the glycine standard is omitted and the quantity of pure water is increased to 3.0 ml. The absorbance is then measured at 570 nm as per 4) above.
6) The actual absorbance produced by the compound under assessment, hereafter called the corrected absorbance, is obtained by subtracting the absorbance of the blank sample from the glycine standard absorbance.

As the degree of activity of compound X is unknown, the method of the above Protocol is preferably repeated a number of times, each time gradually increasing the concentration of compound X. The concentration of compound X is to be increased until the corrected absorbance falls between 0.6 and 0.7. The maximum corrected absorbance possible when using glycine as a control is between 0.75 and 0.80, so no advantage will necessarily be gained in this Protocol assessment by increasing the concentration of the compound any further if a corrected absorbance of 0.6 to 0.7 is achieved.

If the corrected absorbance never exceeds 0.2, this indicates that compound X does not have the degree of activity required for use in the ninhydrin reagent of the present invention.

If the corrected absorbance falls below 0.2 but increasing the concentration of compound X causes it to precipitate out of solution, or causes some other adverse effect, this indicates that compound X does not have the properties required for use in the ninhydrin reagent of the present invention.

Example 2

Protocol 2

Provided, compound X is sufficiently active at elevated temperatures to meet the requirements of Protocol 1 set out in Example 1 above, the following Protocol may be used to assess the long term stability of a ninhydrin reagent comprising compound X at room temperature and in the presence of air.

A ninhydrin reagent is prepared in a similar way to Protocol 1 of Example 1 and stored at room temperature in the presence of air. At set time intervals, a sample is taken from the ninhydrin reagent, mixed with an amino acid solution and heated to 100° C. for a set time. The amount of Ruhemann's purple produced, if any, is measured in terms of an absorbance value. The rate of decrease in intensity of coloration (absorbance) in successive samples indicates whether the long term stability of compound X is adequate for forming part of the ninhydrin reagent of the present invention.

As per Protocol 1, glycine is used as the standard amino acid as the relative sensitivities of other amino acids and amine compounds will be similar whatever reagent is used. The Protocol 2 of the present invention is comprised of the following steps;

1) On day one prepare the following solutions:
   i) A standard 1.0 mM solution of glycine in water.
   ii) A ninhydrin reagent comprising a 1M lithium, sodium or potassium acetate/acetic acid aqueous buffer at between pH 5.2 and 5.3, containing 2% ninhydrin w/v and a chosen concentration (w/v or v/v) of compound X. The concentration of compound X is preferably similar to that identified in Protocol 1 as the concentration at which a corrected absorbance of between 0.2 and 0.7 is achieved. However, as long as the absorbance falls between these two figures, the actual starting concentration of X is not important as this test measures the relative decrease in colour over time. In order to last the full length of the stability trial, at least 250 ml of the reagent should be prepared.

2) On day one, to a standard test tube, add in succession, 2.0 ml of the ninhydrin reagent (ii), 0.20 ml of the glycine standard (i) and 2.8 ml of pure water. Mix and place the test tube in a liquid heating bath at 100 C.° and leave undisturbed for 35 minutes. Take out the test tube and cool quickly to room temperature. Measure the absorbance of the test tube solution in a spectrophotometer at 570 nm against pure water using a flow cell with 1 cm path length.

3) On day one, prepare a blank test tube sample comprising 2.0 ml of reagent (ii) and 3.0 ml of pure water. This will take into account any amino acid or amine type impurities that could be present in the components used to make up the reagents. Mix and place the blank test tube in a heating bath at 100 C.° and leave undisturbed for 35 minutes. Take out the test tube and cool quickly to room temperature. Measure the absorbance of the test tube solution in a spectrophotometer at 570 nm against pure water using a flow cell with 1 cm path length.

4) On day one calculate the corrected absorbance produced by compound X. This is obtained by subtracting the absorbance of the blank sample from the glycine sample absorbance, as described in Protocol 1 of Example 1

5) On day one, after steps 1 to 4 have been completed, store the reagent in a stoppered bottle at 20° C. in the dark and exposed to the air. This is achieved by leaving a large air gap approximately the same volume as the reagent in the bottle.

6) Every two to four weeks, take a sample of the reagent and repeat steps 2 and 3. Each time, calculate the corrected absorbance at 570 nm as per step 4 and compare it with that taken at day one.

Example 3

Selected Chromatography Examples

As discussed above, in relation to the second aspect of the present invention, a wide range of temperature-dependent reducing agents have been identified using protocols 1 and 2 as being sufficiently inactive in reducing ninhydrin to hydrindantin at a first temperature and sufficiently active at reducing ninhydrin to hydrindantin at a second threshold temperature. Further, although this wide range of temperature-dependent reducing agents vary quite significantly in terms of their reducing activity, all are particularly suited to use according to the method of the first aspect of the present invention.

The relative sensitivities of a number of ninhydrin reagents comprising different temperature-dependent reducing agents has been assessed using glycine as a reference amino acid on a standard amino acid analyser, either one produced commercially or one based on the same arrangement as a commercial instrument. The heating system has been modified to include a two stage heating arrangement as discussed above in the first aspect of the present invention. The two stage heating system used to analyse glycine in these chromatography examples is described in more detail below having regard to FIG. 1.

It has been found that a number of organic solvents used to maintain the solubility of commercially available ninhydrin reagents comprising hydrindantin are suitable temperature dependent reducing agents when used according to the method of the present invention. The organic solvents identified were found to have the minimum degree of reducing activity required, although this is relatively weak in comparison to the majority of other compounds deemed suitable temperature dependent reducing agents. Accordingly, higher concentrations and reaction temperatures were expected to be required during use according to the method of the present invention. Alternatively, in order to optimise the reaction conditions, a combination of an organic solvent with temperature-dependent reducing properties and a smaller concentration of a compound with stronger temperature dependent reducing properties may be employed.

It has further been found that ninhydrin reagents containing no organic solvent(s) work just as effectively when used according to the method of the present invention. As discussed in the introduction, such ninhydrin reagents, when used according to the method of the present invention comprising a two stage heating system, can provide sensitivities approaching those reagents comprising an organic solvent.

The chromatography examples below show the sensitivity of ninhydrin reagents either comprising a temperature dependent reducing agent according to the present invention in the presence of an organic solvent; a temperature dependent reducing agent according to the present invention in the absence of organic solvent, or no active compound other than an organic solvent. Further, the dwell time in the heating zone has been varied to illustrate the effect on relative sensitivities. The relative sensitivities for the different examples can be compared accurately as the retention time and peak width at half height is constant for all examples.

It should also be pointed out that the concentration of compound X which satisfies Protocol 1 may not be exactly the concentration that will give optimum performance on the analytical instrument. Protocol 1 provides only a quantitative measure of the activity of a compound X which will be suitable for use on an instrument such as an automated amino acid analyser. A mixture of compounds X can also be used as shown in the following examples, where one of the compound X is an organic solvent. Accordingly, the concentration or concentrations provided by the test Protocol are only be used as a guide for optimizing the sensitivity required on the analytical system and may therefore be varied together with the reaction times and temperatures. The actual contribution of the solvent in these examples, will depend on its concentration, the preheating time and the temperatures of the preheating and colour forming stages. For simplicity, the temperature of the preheating and colour forming stages are the same in the following examples. However, it is to be appreciated that individually varying the temperatures and dwell times of the reactions will significantly increase the scope and versatility of the two stage heating system.

DESCRIPTION OF THE DRAWINGS

FIG. 1 shows a schematic representation of one embodiment of an apparatus for carrying out the method of the present invention.

DETAILED DESCRIPTION OF EXAMPLES OF THE INVENTION

Instrument Conditions

One embodiment of a system for carrying out the method of the present invention is shown in FIG. 1.

With reference to FIG. 1, there is shown an amino acid analyser for carrying out the method of the present invention, generally indicated as 2. The amino acid analyser 2 does not show the means for separating the amino acid sample into its constituent components. However, as discussed above, various known techniques for separating amino acids may be employed. The amino acid analyser 2 comprises a heating zone 4 and a contact zone 6, each consisting of one or more heated reaction coils 7. The heating zone 4 and contact zone 6 are arranged according to a preferred embodiment of the present invention, wherein the heating zone 4 is contained within a separate chamber or vessel to that of the contact zone 6 and is located upstream of the contact zone 6. In an alternative arrangement, the heating zone 4 and the contact zone 6 may be within a single chamber or vessel, with the heating zone 4 comprising an upstream region of the chamber or vessel and the contact zone 6 comprising a downstream region of the chamber or vessel.

The amino acid analyser 2 further comprises a first feed line 8. The first feed line 8 is upstream of the heating zone 4 and is used to deliver the ninhydrin reagent components of the present invention into the amino acid analyser 2. In this embodiment, the ninhydrin reagent components are delivered to the heating zone 4 together as a mixture. The heating zone 4 heats the ninhydrin reagent of the present invention to an elevated temperature for a pre-determined period of time, that is the dwell time of the reagents within the heating zone 4. The activated ninhydrin reagent, that is the ninhydrin reagent comprising hydrindantin, is then delivered to the contact zone 6.

The amino acid analyser 2 further comprises a second feed line 10. The second feed line 10 delivers the nitrogen-containing compounds (in the case of Example 3, this is glycine) from the chromatography column into the amino acid analyser 2. The second feed line 10 delivers the nitrogen-containing compounds to a site downstream of the heating zone 4 but upstream of the contact zone 6, indicated as 12. In an alternative embodiment indicated as 14, the second input 10 delivers the nitrogen-containing compounds directly to the contact zone 6.

The contact zone 6 heats the activated ninhydrin reagent and nitrogen-containing compounds to an elevated temperature for a predetermined period of time. The reaction products are delivered to a photometer 16 where the concentration and characteristics of the nitrogen-containing compounds is detected.

As described above, the heating zone pre-heats only the ninhydrin reagent before it is mixed with the separation column effluent and enters the contact zone. Thus, hydrindantin is produced before the mixing occurs. As shown by the results set out below, the reaction time in the contact zone has no effect on chromatography performance.

Instrument Conditions
Chromatographic mode—Isocratic
Column flow rate 0.45 ml/min
Ninhydrin reagent flow rate—0.30 ml/min
Temperature of pre-heating chamber—Variable between 125 and 135° C., depending on activity of compound used
Temperature of heated colour forming reaction chamber—Same as pre-heating chamber for all examples
Pre-heater reaction time—30 or 60 seconds
Colour forming heater reaction time—60 seconds
Injection volume—20 µl
Amount of glycine injected—2 nmoles
Retention time—5.0 minutes
Peak width at half height of 0.26 minutes
Sensitivity scale—1 mAU is equivalent to 0.001 absorbance
Reagent Conditions
1M sodium acetate/acetic acid buffer adjusted to pH 5.2 (lithium or potassium based buffers can also be used), containing 2% w/v ninhydrin. For the concentration of temperature-dependent reducing agent or agents please refer to the specific examples.
Examples with 30 Second Pre-Heating Time and 60 Second Heated Colour Reaction Time As shown in Examples 1 and 2, ethylene glycol, when pre-heated for 30 seconds does not function as temperature-dependent reducing agent. Accordingly in these examples, ethylene glycol is acting as an organic solvent only.

Example 1

The sensitivity of a ninhydrin reagent comprising 1% sodium formate w/v as temperature-dependent reducing agent and 40% ethylene glycol was assessed according to the method of the present invention.

The ninhydrin reagent was pre-heated in the heating zone for 30 seconds and reacted with the eluent in the contact zone for 60 seconds. The reaction temperature in both the heating zone and contact zone was set to 128° C.

Using the above conditions, a peak height of 153 mAU was observed.

Example 2

The sensitivity of a ninhydrin reagent comprising 2% glucose w/v as temperature-dependent reducing agent and 40% ethylene glycol was assessed according to the method of the present invention.

The ninhydrin reagent was pre-heated in the heating zone for 30 seconds and reacted with the eluent in the contact zone for 60 seconds. The reaction temperature in both the heating zone and contact zone was set to 130° C.

Using the above conditions, a peak height of 150 mAU was observed.

Example 3

The sensitivity of a ninhydrin reagent comprising 2% glucose w/v as temperature-dependent reducing agent and no organic solvent was assessed according to the method of the present invention.

The ninhydrin reagent was pre-heated in the heating zone for 30 seconds and reacted with the eluent in the contact zone for 60 seconds. The reaction temperature in both the heating zone and contact zone was set to 130° C.

Using the above conditions, a peak height of 140 mAU was observed.

Examples with 60 Seconds Pre-Heating Time and 60 Seconds Heated Colour Reaction Time As shown in Examples 4 and 6, ethylene glycol when pre-heated for 60 seconds is capable of acting as a temperature-dependent reducing agent. In these examples, ethylene glycol is also functioning as an organic solvent.

Example 4

The sensitivity of a ninhydrin reagent comprising 1% glucose w/v as temperature-dependent reducing agent and 40% ethylene glycol was assessed according to the method of the present invention.

The ninhydrin reagent was pre-heated in the heating zone for 60 seconds and reacted with the eluent in the contact zone for 60 seconds. The reaction temperature in both the heating zone and contact zone was set to 132° C.

Using the above conditions, a peak height of 140 mAU was observed.

Example 5

The sensitivity of a ninhydrin reagent comprising 0.2% glucose w/v as temperature-dependent reducing agent and no organic solvent was assessed according to the method of the present invention.

The ninhydrin reagent was pre-heated in the heating zone for 60 seconds and reacted with the eluent in the contact zone for 60 seconds. The reaction temperature in both the heating zone and contact zone was set to 134° C.

Using the above conditions, a peak height of 129 mAU was observed.

Example 6

The sensitivity of a ninhydrin reagent comprising 50% ethylene glycol and no other temperature-dependent reducing agent was assessed according to the method of the present invention.

The ninhydrin reagent was pre-heated in the heating zone for 60 seconds and reacted with the eluent in the contact zone for 60 seconds. The reaction temperature in both the heating zone and contact zone was set to 134° C.

Using the above conditions, a peak height of 133 mAU was observed.

SUMMARY

The above chromatography examples illustrate that the method of the present invention provides extra versatility and scope in terms of the number of temperature-dependent reducing agents that can be used. In addition, higher sensitivities can be achieved, in some cases with lower concentrations of temperature dependent reducing agents and/or lower reaction temperatures. When considering the 30 second pre-heating coil the increased sensitivity becomes immediately apparent when compared to a one stage heating system under similar conditions, with a 55% increase for the glucose and ethylene glycol reagent and a 77% increase for glucose with no ethylene glycol.

When the 60 second pre-heater is used the organic solvent, ethylene glycol, becomes much more active at the 40% v/v level and above and can now act as both a temperature dependent reducing agent and an organic solvent. Therefore in combination with ethylene glycol, lower concentrations of the more active ingredients such as glucose can be used and 50% ethylene glycol on its own gives good sensitivity. Another notable result is Example 5 where a lower concentration of glucose with no organic solvent gives good sensitivity at 134° C.

The invention claimed is:

1. A method for analysing one or more nitrogen-containing compounds, in which the one or more nitrogen-containing compounds are contacted with hydrindantin at an elevated temperature in a contact zone, the method comprising:
    contacting ninhydrin with one or more reducing agents in a heating zone for a reaction time in the heating zone at a first elevated temperature to produce a hydrindantin-containing mixture, wherein the ninhydrin and the one or more reducing agents are provided in the form of a ninhydrin reagent, said ninhydrin reagent being essentially free from hydrindantin, the ninhydrin reagent comprising:
    ninhydrin;
    an aqueous buffer, the ninhydrin reagent having a pH, wherein the buffer maintains the pH at a value between 4.5 to 5.5; and
    a temperature-dependent reducing agent present in a concentration, which agent is inactive in the reduction of ninhydrin at a first temperature, wherein the first temperature is no greater than 30° C., and active in reducing ninhydrin to hydrindantin at a second temperature, wherein the second temperature is higher than the first temperature and is at least 100° C., and wherein the second temperature is equal to or greater than said first elevated temperature; and
    introducing the hydrindantin-containing mixture into the contact zone and contacting the hydrindantin-containing mixture with the nitrogen-containing compounds for a reaction time in the contact zone at a second elevated temperature.

2. The method according to claim 1, wherein the heating zone and contact zone are housed within separate chambers.

3. The method according to claim 1, wherein the contact zone is located downstream of the heating zone.

4. The method according to claim 1, wherein the heating zone and the contact zone are operated at the same temperature.

5. The method according to claim 1, wherein the temperature within the heating zone and/or the contact zone is from 120° C. to 135° C.

6. The method according to claim 1, wherein the ninhydrin and the reducing agent are heated in the heating zone for a period of from 30 to 60 seconds.

7. The method according to claim 1, wherein the hydrindantin-containing mixture has a residence time in the contact zone of from 30 to 60 seconds.

8. The method according to claim 1, wherein there is a rate of hydrindantin production in the method, wherein the rate of hydrindantin production is controlled by changing one or more parameters selected from the group consisting of a concentration of the reducing agent, a reaction time in the heating zone, a reaction time in the contact zone, the temperature within the heating zone, and the temperature in the contact zone.

9. The method according to claim 1, wherein the first temperature is from 10° C. to 20° C.

10. The method according to claim 1, wherein the temperature-dependent reducing agent is a compound having an activity of at least 50% of its initial activity after 24 months.

11. The method according to claim 1, wherein the temperature-dependent reducing agent comprises one or more saccharides.

12. The method reagent according to claim 11, wherein the temperature-dependent reducing agent comprises a compound selected from the group consisting of: Glucose, Fructose, Glyceraldehyde, Galactose, Ribose, Xylose, Erythrose, Threose, Lyxose, Arabinose, Allose, Altrose, Mannose, Gulose, Idose, Talose and L-Glycero-D-manno-heptose, Dihydroxyacetone, Erythrulose, Ribulose, Xylulose, Psicose, Sorbose, Tagatose, Sedoheptalose, or a mixture thereof; Lactose, Maltose, Trihalose, Cellobiose, Kojibiose, Nigerose, Isomaltose, Sophorose, Sucrose, Laminaribiose, Gentiobiose, Turanose, Maltulose, Palatinose, Gentiobiulose, Mannobiose, Melibiose, Melibiulose, Rutinose, Xylobiose or a mixture thereof; and Stachyose, Dextrin, Maltodextrin, or a mixture thereof.

13. The method according to claim 1, wherein the temperature-dependent reducing agent comprises one or more carboxylic acids and/or a salt thereof.

14. The method according to claim 13, wherein the carboxylic acid is formic acid or a salt thereof.

15. The method according to claim 1, wherein the temperature-dependent reducing agent comprises citric acid or tartaric acid.

16. The method according to claim 1, wherein the temperature-dependent reducing agent comprises one or more compounds having one or more aldehyde and/or ketone groups.

17. The method according to claim 16, wherein the temperature-dependent reducing agent comprises acetone.

18. The method according to claim 1, wherein the temperature-dependent reducing agent comprises a sulfite, thiosulfate, a phosphite and/or a hypophosphite or a mixture thereof.

19. The method according to claim 1, wherein the temperature-dependent reducing agent comprises an alcohol having one or more hydroxyl groups.

20. The method according to claim 19, wherein the temperature-dependent reducing agent comprises an alcohol selected from the group consisting of: methanol, ethanol, propanol, polyethylene glycol, ethylene glycol, propylene glycol, mannitol and sorbitol or a mixture thereof; and a compound selected from the group consisting of methoxy ethanol, propylene glycol monomethyl ether, carbitol, dimethylsulfoxide or sulfolane or a mixture thereof.

21. The method according to claim 1, wherein the concentration of the temperature-dependent reducing agent is from 0.01% to 20% w/v or v/v.

22. The method according to claim 1, wherein the concentration of ninhydrin in the ninhydrin reagent is from 1 to 2.5% w/v or v/v.

23. The method according to claim 1, wherein the buffer comprises acetic acid, ethanoic acid or propanoic acid.

24. The method according to claim 1, wherein the ninhydrin reagent further comprises one or more organic solvents.

25. The method according to claim 24, wherein the organic solvent comprises a compound selected from the group consisting of: dimethylsulfoxide, ethylene glycol, propylene glycol, sulfolane, carbitol, propylene glycol monomethyl ether, methylcellosolve and methanol or a mixture thereof.

26. The method according to claim 25, wherein the concentration of organic solvent is from 35% to 55% v/v.

* * * * *